US007916836B2

(12) United States Patent
Tkaczyk et al.

(10) Patent No.: US 7,916,836 B2
(45) Date of Patent: Mar. 29, 2011

(54) METHOD AND APPARATUS FOR FLEXIBLY BINNING ENERGY DISCRIMINATING DATA

(75) Inventors: John Eric Tkaczyk, Delanson, NY (US); James Wilson Rose, Guilderland, NY (US); Wen Li, Clifton Park, NY (US); Jonathan D. Short, Saratoga Springs, NY (US); Yanfeng Du, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 64 days.

(21) Appl. No.: 11/861,826

(22) Filed: Sep. 26, 2007

(65) Prior Publication Data

US 2009/0080601 A1 Mar. 26, 2009

(51) Int. Cl.
*H05G 1/64* (2006.01)
*H01L 27/146* (2006.01)
(52) U.S. Cl. ............... 378/98.8; 378/19; 250/370.09
(58) Field of Classification Search ............ 378/19, 378/98.8; 250/370.09
See application file for complete search history.

(56) References Cited

U.S. PATENT DOCUMENTS

| 5,336,879 | A | * | 8/1994 | Sauer | 250/208.1 |
| 5,352,897 | A | * | 10/1994 | Horikawa et al. | 250/370.06 |
| 5,464,984 | A | * | 11/1995 | Cox et al. | 250/370.11 |
| 6,522,715 | B2 | * | 2/2003 | Hoffman et al. | 378/19 |
| 6,744,912 | B2 | * | 6/2004 | Colbeth et al. | 382/132 |
| 7,145,985 | B2 | * | 12/2006 | Strommer | 378/98.8 |
| 7,223,981 | B1 | * | 5/2007 | Capote et al. | 250/370.13 |
| 2002/0085665 | A1 | * | 7/2002 | Hoffman et al. | 378/19 |
| 2005/0286682 | A1 | * | 12/2005 | Tkaczyk et al. | 378/98.8 |
| 2006/0056581 | A1 | * | 3/2006 | Hoffman et al. | 378/19 |
| 2007/0120062 | A1 | * | 5/2007 | Li et al. | 250/370.09 |

* cited by examiner

*Primary Examiner* — Edward J Glick
*Assistant Examiner* — Thomas R Artman
(74) *Attorney, Agent, or Firm* — Jason K. Klindtworth (57) ABSTRACT

A CT detector includes a direct conversion material configured to generate electrical charge upon reception of x-rays, a plurality of metallized anodes configured to collect electrical charges generated in the direct conversion material, at least one readout device, and a redistribution layer having a plurality of electrical pathways configured to route the electrical charges from the plurality of metallized anodes to the at least one readout device. A plurality of switches is coupled to the plurality of electrical pathways between the plurality of metallized anodes and the at least one readout device, wherein each of the plurality of switches includes an input line electrically coupled to one of the plurality of metallized anodes, a first output node electrically coupled to the at least one readout device, and a second output node electrically coupled to at least one other switch of the plurality of switches.

13 Claims, 8 Drawing Sheets

METHOD AND APPARATUS FOR FLEXIBLY BINNING ENERGY DISCRIMINATING DATA

BACKGROUND OF THE INVENTION

The present invention relates generally to diagnostic imaging and, more particularly, to a method and apparatus of photon counting with a detector having a combined pixel size and shared charge-sharing boundaries during low flux, and having unshared pixels in a portion of the detector when the portion is experiencing a high flux.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about a gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

While it is generally recognized that CT imaging would not be a viable diagnostic imaging tool without the advancements achieved with conventional, scintillator-based CT detector design, a drawback of these detectors is their inability to provide energy discriminatory data or otherwise count the number and/or measure the energy of photons actually received by a given detector element or pixel. That is, the light emitted by the scintillator is a function of the number of x-rays impinged as well as the energy level of the x-rays. Under the charge integration operation mode where x-rays impinge upon a pixel and the charge generated therein is integrated over time, the photodiode is not capable of discriminating between the energy level and the photon count from the scintillation. For example, two scintillators may illuminate with equivalent intensity and, as such, provide equivalent light output to their respective photodiodes; yet, the number of x-rays received by each scintillator may be different as well as the intensity of each of the x-rays.

Recent detector developments have included the design of an energy discriminating, direct conversion detector that can provide photon counting and/or energy discriminating feedback with high spatial resolution. In this regard, the detector can be caused to operate in an x-ray counting mode, an energy measurement mode of each x-ray event, or both. These energy discriminating, direct conversion detectors are capable of not only x-ray counting, but also providing a measurement of the energy level of each x-ray detected. While a number of materials may be used in the construction of a direct conversion energy discriminating detector, semiconductors have been shown to be one preferred material.

A drawback of direct conversion semiconductor detectors, however, is that these types of detectors cannot count at the x-ray photon fluxes typically encountered with conventional CT systems, e.g. at or above $10^6$ counts per sec per millimeter squared. Saturation can occur at detector locations wherein small subject thickness is interposed between the detector and the radiographic energy source or x-ray tube. These saturated regions correspond to paths of low subject thickness near or outside the width of the subject projected onto the detector fan-arc. In many instances, the subject is more or less circular or elliptical in the effect on attenuation of the x-ray flux and subsequent incident intensity to the detector. In this case, the saturated regions represent two disjointed regions at extremes of the fan-arc. In other less typical, but not rare instances, saturation occurs at other locations and in more than two disjointed regions of the detector. In the case of an elliptical subject, the saturation at the edges of the fan-arc is reduced by imposing a bowtie filter between the subject and the x-ray source. Typically, the filter is constructed to match the shape of the subject in such a way as to equalize total attenuation, filter and subject, across the fan-arc. The flux incident to the detector is then relatively uniform across the fan-arc and does not result in saturation.

What can be problematic, however, is that the bowtie filter may not be optimal given that a subject population is significantly less than uniform and not exactly elliptical in shape. In such cases, it is possible for one or more disjointed regions of saturation to occur or conversely to over-filter the x-ray flux and create regions of very low flux. Low x-ray flux in the projection will ultimately contribute to noise in the reconstructed image of the subject.

The very high x-ray photon flux encountered in CT detectors, i.e., above a threshold of approximately $10^6$ counts per sec per millimeter squared, causes pile-up and polarization which ultimately leads to detector saturation. That is, these detectors typically saturate at relatively low x-ray flux level thresholds. Above this threshold, the detector response is not predictable or has degraded dose utilization. Detector saturation causes loss of imaging information and results in artifacts in x-ray projection and CT images. In addition, hysteresis and other non-linear effects occur at flux levels near detector saturation as well as flux levels over detector saturation.

"Pile-up" is a phenomenon that occurs when a source flux at the detector is so high that there is a non-negligible possibility that two or more X-ray photons deposit charge packets in a single pixel close enough in time so that their signals interfere with each other. Pile-up phenomenon can generally be categorized in two general types, which result in somewhat different effects. In the first type, the two or more events are separated by sufficient time so that they are recognized as distinct events, but the signals overlap so that the precision of the measurement of the energy of the later arriving x-ray or x-rays is degraded. This type of pile-up results in a degradation of the energy resolution of the system. In the second type of pile-up, the two or more events arrive close enough in time so that the system is not able to resolve them as distinct events. In such a case, these events are recognized as one single event having the sum of their energies and the events are shifted in the spectrum to higher energies. In addition, pile-up leads to a more or less pronounced depression of counts in high x-ray flux, resulting in detector quantum efficiency (DQE) loss.

Direct conversion detectors are also susceptible to a phenomenon called "polarization" where charge trapping inside the material changes the internal electric field, alters the detector count and energy response in an unpredictable way, and results in hysteresis where response is altered by previous exposure history.

For Cadmium Zinc Telluride (CZT) or Cadmium Telluride (CdTe), which are two possible direct conversion materials used for x-ray spectroscopy, an x-ray flux saturation limit of $10^7$ counts per sec per millimeter squared is generally found for pixel size on the order of 1.0 mm and thicknesses of order 3.0-5.0 mm. This limit is directly related to the charge collection time for CZT. Higher fluxes are possible using smaller pixels. Each pixel has a size-independent count rate limit set by the charge collection time. The saturation flux is thereby set by the count rate limit divided by the area of the pixel. Therefore, the saturation flux increases as the pixel size decreases. Smaller pixels are also desirable because they make available higher spatial resolution information which can result in high resolution images. However, small pixel size results in higher cost and there are more channels per unit area which need to be connected to readout electronics.

In addition, smaller pixels or detector elements have larger perimeter to area ratios resulting in more cross-talk. The perimeter is a region where charge is shared between two or more pixels, therefore resulting in cross-talk. This sharing of charge results in incomplete energy information and/or a miscount of x-ray photons because the readout electronics are not typically configured to combine simultaneous signals in neighboring pixels. A system may be configured to sense for coincidence of photon arrival events on neighboring channels and record only one count in such a case, but such a system suffers from the chance coincidence of two or more real counts falling on neighboring pixels, thus leading to loss of DQE at high count rates.

Detector saturation can affect image quality by constraining the number of photons used to reconstruct the image and by introducing image artifacts. A minimum image quality (therefore, a minimum flux) is required to make use of the images. In this regard, when setting the configuration of the system such that sufficient flux is received at one area of the detector, it is likely that another area of the detector will receive higher flux, and possibly, flux high enough to saturate the detector in this area. Higher flux in these other areas may not be necessary for image quality, and the loss of data due to detector saturation may need to be addressed through correction algorithms in order to reduce image artifacts. For CT imaging, the reconstruction is not tolerant of missing or corrupted data. For example, if the center of the detector is illuminated with a minimum flux for image quality purposes, and if the illuminated object is compact, then detector cells at and beyond the periphery of the object's shadow can be saturated due to thin object thickness in these projected directions. The reconstruction of the data set with these uncorrected saturated values will cause severe artifacts in the image.

A number of imaging techniques have been developed to address saturation of any part of the detector. These techniques include maintenance of low x-ray flux across the width of a detector array, for example, by using low tube current or current that is modulated per view. However, this solution leads to increased scan time. That is, there is a penalty that the acquisition time for the image is increased in proportion to the nominal flux needed to acquire a certain number of x-rays that meet image quality requirements.

Furthermore, the flux capability of a photon-counting system can be improved by decreasing the pixel element area. However, to increase the flux capability of the pixels to a level required during CT imaging, the pixel area would have to be decreased to such a size that the total pixel count, thus the number of interconnects and DAS channels, would be prohibitively large and impractical as a solution.

Therefore, it would be desirable to design a method and apparatus to have a large pixel size and a reduced number of charge-sharing boundaries in a CT detector during low flux, and to have a small non-saturating pixel size in a portion of the CT detector when the portion is experiencing a high flux.

BRIEF DESCRIPTION OF THE INVENTION

The present invention is directed to a method and apparatus that overcome the aforementioned drawbacks. A detector is configured to have a large pixel size and a reduced number of charge-sharing boundaries in a CT detector during low flux, and to have a small non-saturating pixel size in a portion of the CT detector when the portion is experiencing a high flux.

Therefore, according to one aspect of the present invention, a CT detector includes a direct conversion material configured to generate electrical charge upon reception of x-rays, a plurality of metallized anodes configured to collect electrical charges generated in the direct conversion material, at least one readout device, and a redistribution layer having a plurality of electrical pathways configured to route the electrical charges from the plurality of metallized anodes to the at least one readout device. A plurality of switches is coupled to the plurality of electrical pathways between the plurality of metallized anodes and the at least one readout device, wherein each of the plurality of switches includes an input line electrically coupled to one of the plurality of metallized anodes, a first output node electrically coupled to the at least one readout device, and a second output node electrically coupled to at least one other switch of the plurality of switches.

In accordance with another aspect of the present invention, a method of fabricating a CT detector includes providing a direct conversion material, attaching a plurality of metallized anodes to the direct conversion material, electrically coupling an input of a first switch to a first anode of the plurality of metallized anodes, and electrically coupling a first output of the first switch to a second anode of the plurality of metallized anodes and to a first readout channel of a readout device.

Yet another aspect of the present invention includes a CT system having a rotatable gantry having an opening to receive an object to be scanned. The CT system includes a high frequency electromagnetic energy projection source configured to project a high frequency electromagnetic energy beam toward the object and a detector positioned to receive x-rays that pass through the object. The detector includes a pair of electrical charge collectors having a gap therebetween, a direct conversion material electrically coupled to the pair of electrical charge collectors, and a readout device having a first input channel coupled to a switch, wherein a first output of the switch is configured to electrically connect one input channel of the readout device to the pair of electrical charge collectors.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
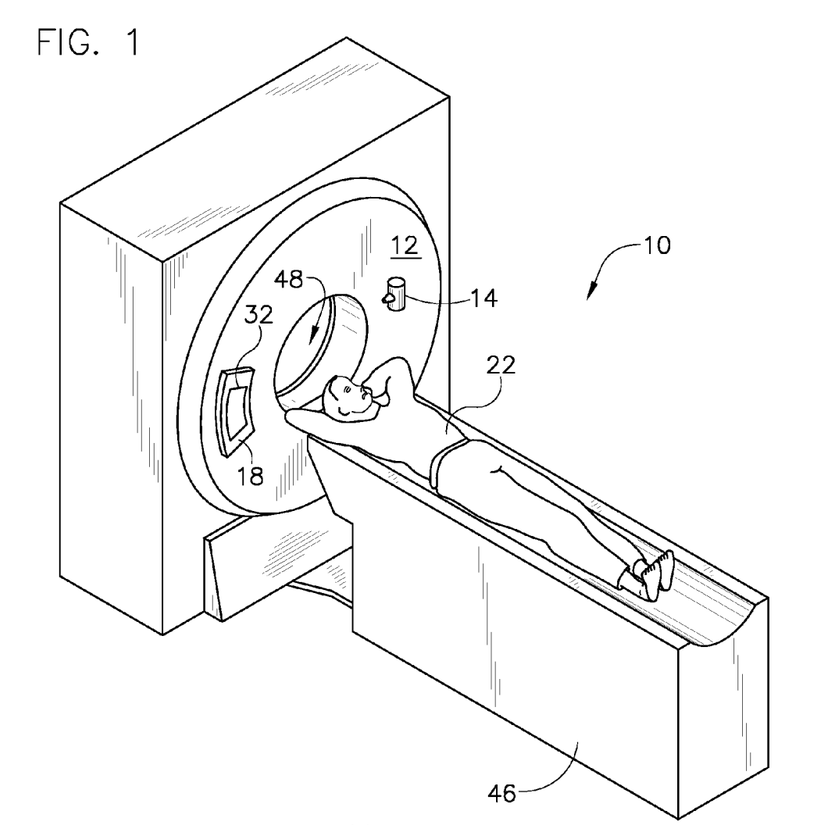
FIG. 1 is a pictorial view of a CT imaging system.
Figure 2:
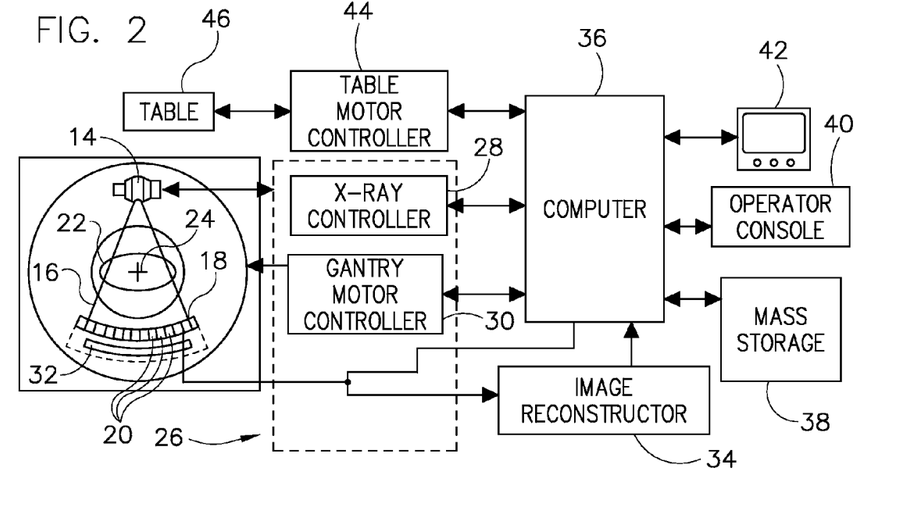
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
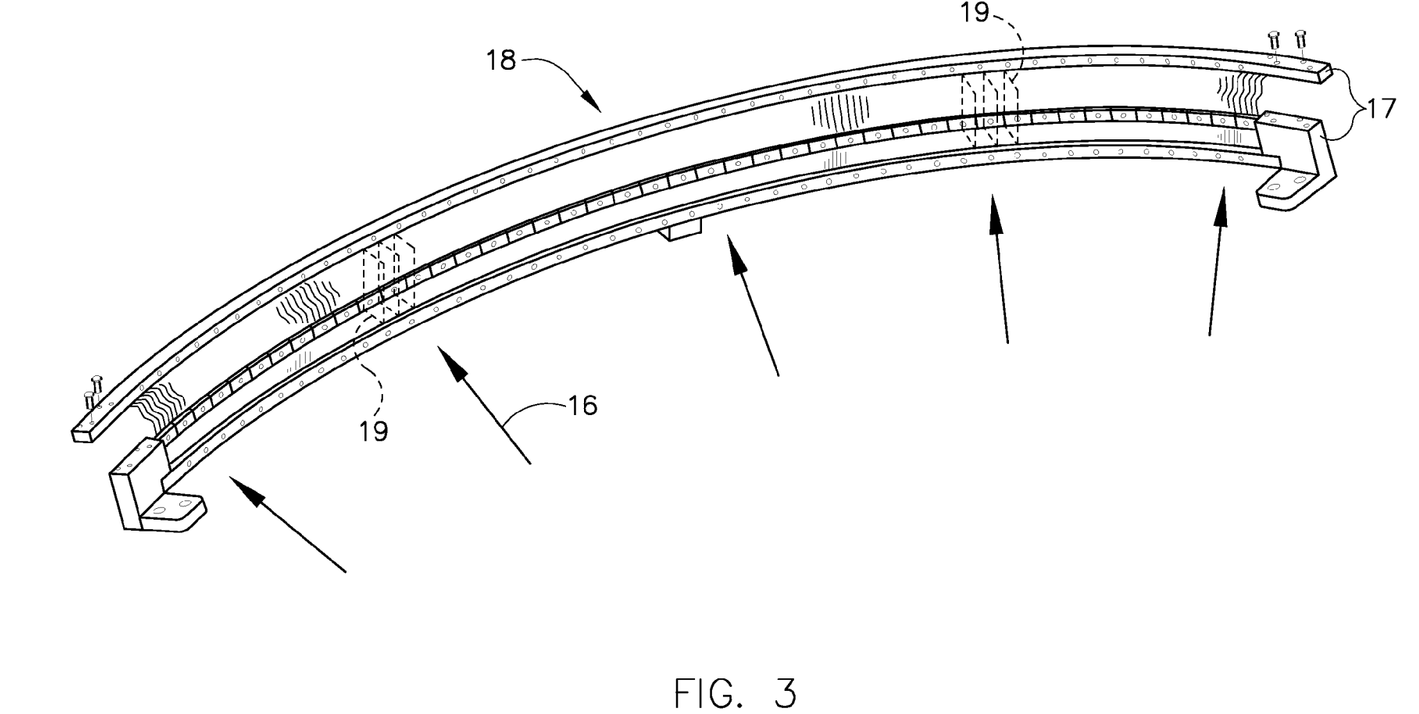
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
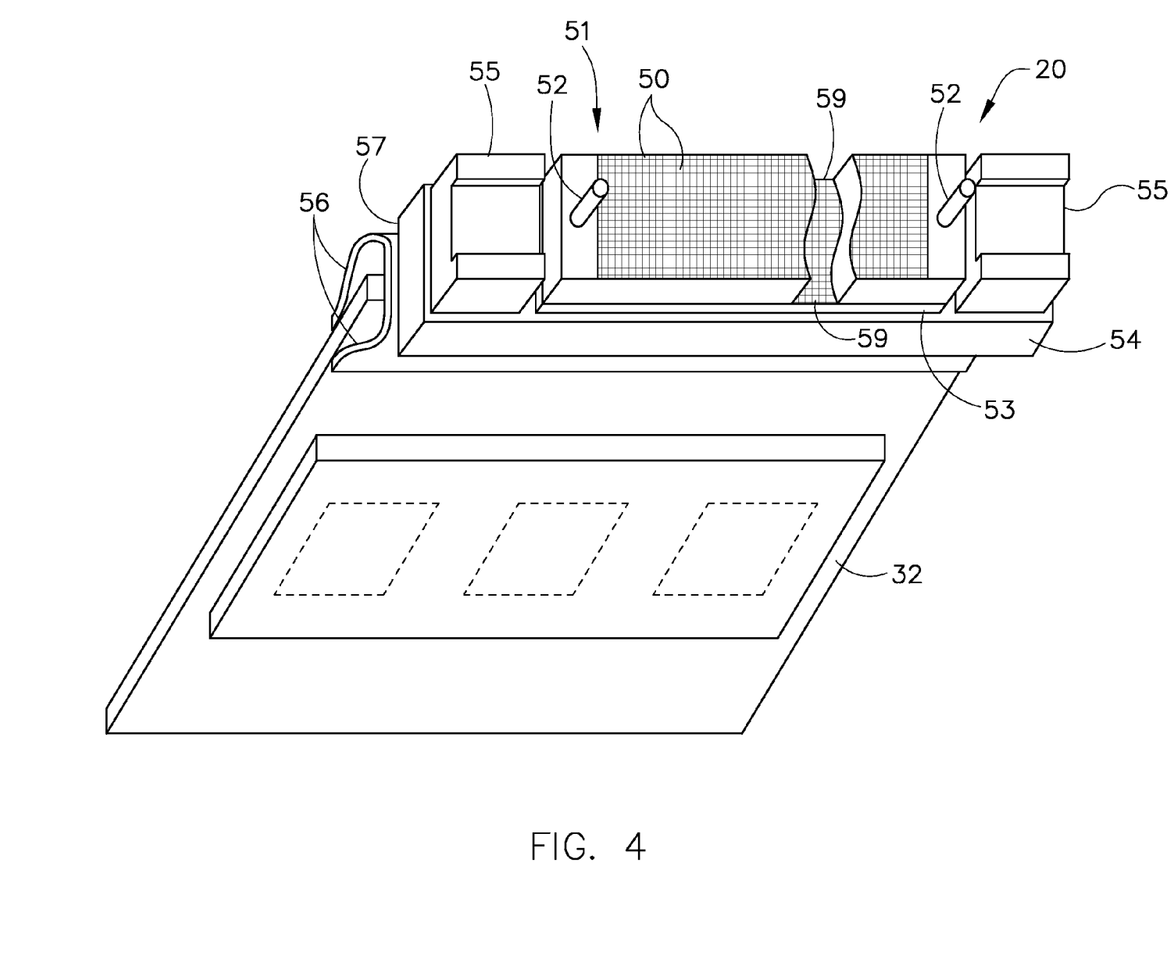
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. Each detector 20 includes a semiconductor layer fabricated from CZT, CdTe, or another direct conversion material. Each detector 20 also includes a plurality of metallized anodes attached to the semiconductor layer.

The detector 20 may include a semiconductor layer having a plurality of pixelated anodes attached thereto. The detector supports not only x-ray photon counting, but energy measurement or tagging as well. As a result, the present invention supports the acquisition of both anatomical detail as well as tissue characterization information. In this regard, the energy discriminatory information or data may be used to reduce the effects of beam hardening and the like. Furthermore, these detectors support the acquisition of tissue discriminatory data and therefore provide diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization.

Pixelated regions of an energy discriminating detector may be combined to form patterns of pixels selected to affect both saturation threshold and cross-talk in a detector array. Specifically, pixels may be combined into a large effective area by using switching elements, for periods of time and in sections of the detector array that are experiencing low flux. Likewise, the switches may be selectively operated to decrease the number of pixels combined within portions of the detector array, thus enabling high flux operation of such pixels within portions of the detector array. Furthermore, pixels within the detector array may be arranged to include single pixels positioned within or contiguous with large pixel arrays to enable a combined operation having portions of the array with high flux capability and having portions of the array with low amounts of charge sharing. Thus, an arrangement of pixels in a detector may be selected in order to optimize detector operation by trading off saturation threshold and cross-talk, while further optimizing and minimizing the total number of DAS channels required to read the entire array.

Figure 5:
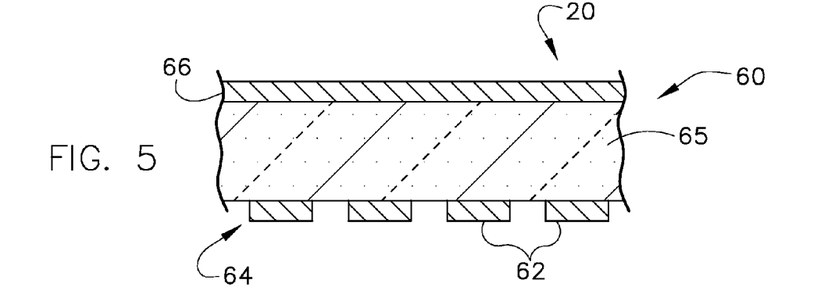
FIG. 5 is a cross-section of a portion of a direct conversion detector.

Referring now to FIG. 5, a cross-section of a portion of a CZT or direct conversion detector 20 in accordance with one embodiment of the present invention is shown. Detector 20 is defined by a semiconductor layer 60 having a number of electronically pixelated structures or pixels to define a number of detector elements, anodes, or contacts 62. This electronic pixelation is accomplished by applying a 2D array 64 of electrical contacts 62 onto a layer 60 of direct conversion material 65.

Detector 20 includes a contiguous high-voltage electrode 66 attached to direct conversion material 65. The high-voltage electrode 66 is connected to a power supply (not shown) and it is designed to power the semiconductor layer 60 during the x-ray detection process. One skilled in the art will appreciate that the high-voltage layer 66 should be relatively thin so as to reduce the x-ray absorption characteristics and, in a preferred embodiment, is a few hundred angstroms in thickness. In a preferred embodiment, the high-voltage electrode 66 may be affixed to the direct conversion material 65 through a metallization process. X-ray photons that impinge upon the direct conversion material 65 will generate an electrical charge therein, which is collected in one or more of the electrical contacts 62, and which may be read out to the DAS 32 of FIG. 2. The amplitude of the charge collected is indicative of the energy of the photon, or photons, that created the charge.

Figure 6:
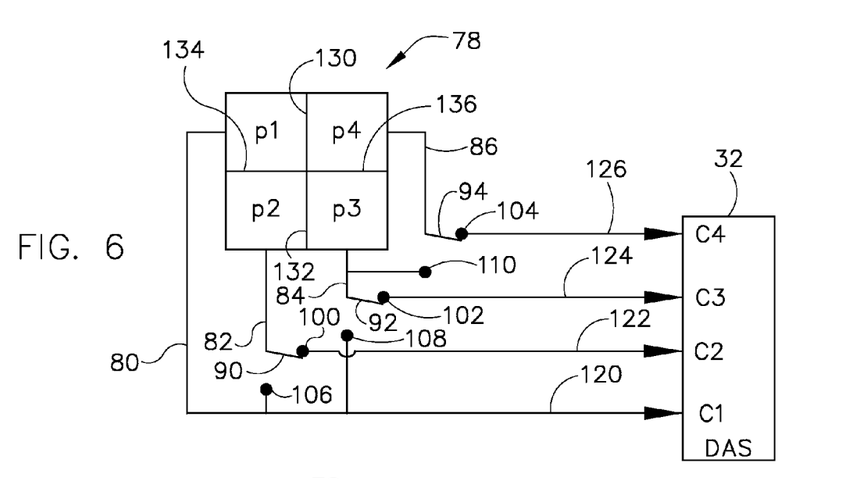
FIG. 6 illustrates four sub-pixels switched to output separate charges per pixel according to an embodiment of the present invention.
Figure 7:
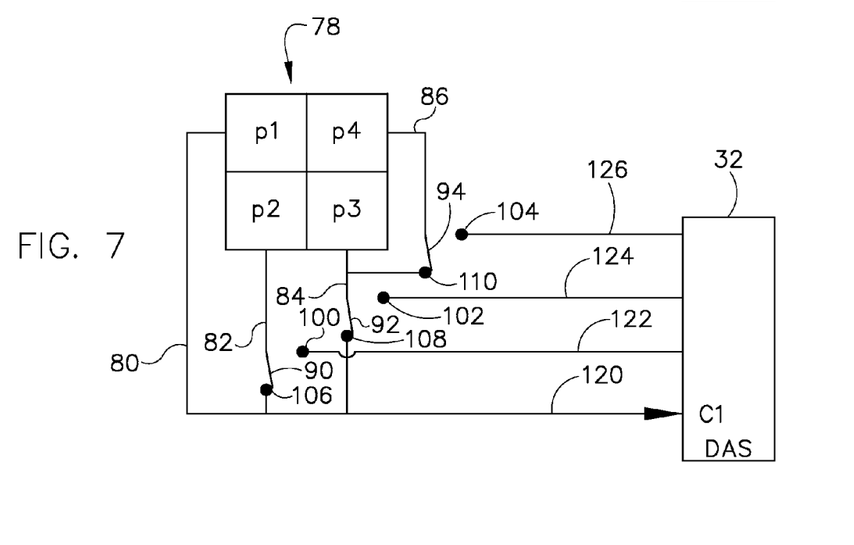
FIG. 7 illustrates four sub-pixels switched to output a single charge according to an embodiment of the present invention.

Pixels may be combined to obtain a large area detector through appropriate switching of readout lines that has a total area equal to a sum of the areas of the combined pixels and the spaces therebetween. Alternatively and through appropriate switching of the readout lines, each pixel may be individually read out. An embodiment of the present invention contemplates any combination of pixels or pixel groups together with any individual pixel readouts. Referring to FIGS. 6 and 7, pixels p1-p4 represent a pattern 78 of electrical contacts such as the electrical contacts 62 of FIG. 5. As shown, each pixel p1-p4 has attached thereto a respective readout line 80, 82, 84, 86. Readout lines 82, 84, and 86 have respective switches 90, 92, and 94 in electrical contact therewith. It is contemplated that switches 90-94 may each comprise one or more semiconductor switching devices such as a field-effect transistor (FET), a bipolar junction transistor (BJT), and the like.

As illustrated, switch 90 may be positioned at either a first node 100 or a second node 106; switch 92 may be positioned at either a first node 102 or a second node 108; and switch 94 may be positioned at either a first node 104 or a second node 110. Furthermore, node 104 is in electrical contact with a readout line 126; node 102 is in electrical contact with a readout line 124; node 100 is in electrical contact with a readout line 122; and nodes 106 and 108 are in electrical contact with a readout line 120.

FIG. 6 illustrates an embodiment of the present invention wherein electrical charges generated in pattern 78 of pixels p1-p4 are each read out to DAS 32 as single or individual charges. Accordingly, switches 90, 92, and 94 are positioned such that charges generated in pixels p1-p4 are directed to individual read out lines 120, 122, 124, and 126. Specifically, switch 90 is positioned at node 100, switch 92 is positioned at node 102, and switch 94 is positioned at node 104. As such, when an electrical charge is generated within pixel p1, the charge generated therein is directed to readout line 80 and to readout line 126 and is output as charge C1 to DAS 32. When an electrical charge is generated within pixel p2, the charge generated therein is directed to readout line 82, through switch 90 to node 100, and to readout line 122 and output as charge C2 to DAS 32. Likewise, when an electrical charge is generated within pixel p3, the charge generated therein is directed to readout line 84, through switch 92 to node 102, and to readout line 124 and output as charge C3 to DAS 32. Furthermore, when an electrical charge is generated within pixel p4, the charge generated therein is directed to readout line 86, through switch 94 to node 104, and to readout line 126 and output as charge C4 to DAS 32.

FIG. 7 illustrates an embodiment of the present invention wherein electrical charges generated in pixels p1-p4 are combined and read out to DAS 32 of FIG. 2 as a single electrical charge collected in pixels p1-p4, thereby forming a single larger pixel area that includes all the areas of pixels p1-p4, and having no charge-sharing region therebetween. In this embodiment, switches 90, 92, and 94 are positioned such that charges generated in pixels p1-p4 are combined into a single charge and read out through electrical line 120. Specifically, switch 90 is positioned at node 106, switch 92 is positioned at node 108, and switch 94 is positioned at node 110. As such, when an electrical charge is generated within pixel p1, the charge generated therein is directed to readout line 80 and to readout line 120 and output to DAS 32. When an electrical charge is generated within pixel p2, the charge generated therein is directed to readout line 82, through switch 90 to node 106, and to readout line 120. Likewise, when an electrical charge is generated within pixel p3, the charge generated therein is directed to readout line 84, through switch 92 to node 108, and to readout line 120. Furthermore, when an electrical charge is generated within pixel p4, the charge generated therein is directed to readout line 86, through switch 94 to node 110, to readout line 84, through switch 92 to node 108, and to readout line 120. As such, electrical charges generated within pixels p1-p4 add to form a single collected charge C1, which is output through electrical line 120 to DAS 32.

Thus, because a pixel has a size-independent count rate limit set by the charge collection time, the saturation flux is thereby set by the count rate limit divided by the area of the pixel. Therefore, the saturation flux is increased for the arrangement of switches as illustrated in FIG. 6. However, though the smaller pixels of FIG. 6 have increased resolution when compared to the arrangement of FIG. 7, the pixels of FIG. 6 exhibit larger perimeter-to-area ratios, which may result in more cross-talk when compared to the arrangement of FIG. 7. Thus, the switches 90-94 may be appropriately selected to optimize resolution, saturation flux, and crosstalk.

Accordingly, FIGS. 6 and 7 illustrate embodiments of the present invention where a first saturation threshold is exhibited in pixels p1-p4 of pattern 78 as illustrated in FIG. 6 and where a second saturation threshold, lower than the first saturation threshold, is exhibited in pixels p1-p4 of pattern 78 as illustrated in FIG. 7. As such, the readout pattern of pixels p1-p4 as illustrated in FIG. 6 each have an increased saturation capability because of the reduced overall area of each pixel, as compared to the readout pattern and, effectively, the larger single pixel as illustrated in FIG. 7.

The positions of switches 90-94 illustrated in FIGS. 6 and 7 result in differing effects of cross-talk as well. Referring again to FIG. 6, charge-sharing regions 130, 132, 134, and 136 occur between neighboring pixels p1-p4. More specifically, charge-sharing region 130 occurs between pixels p1 and p4; charge-sharing region 132 occurs between pixels p2 and p3; charge-sharing region 134 occurs between pixels p1 and p2; and charge-sharing region 136 occurs between pixels p3 and p4. As such, when a charge is generated within the pixel pattern 78 within or near one of the charge-sharing regions 130-136, the pair of neighboring pixels (p1, p4; p2, p3; p1, p2; and p3, p4, respectively) adjacent to the generated charge in the charge-sharing region 130-136 may each partially collect a portion of the generated charge.

In contrast, because output of the pixels p1-p4 are combined in the embodiment illustrated in FIG. 7, charges shared between pixels p1-p4 in the charge-sharing regions 130-136 of FIG. 6 have an increased effect on image quality. Interpixel cross-talk of pixels p1-p4 is read out as a single charge because pixels p1-p4 are effectively combined into a single pixel. Thus, charges generated in the charge-sharing regions 130-136 of FIG. 6 are collected and read out as a single charge, regardless of which pixel anode p1-p4 collected the charge.

One skilled in the art will recognize that the number of pixels need not be a two-by-two arrangement as illustrated in FIGS. 6 and 7 and that embodiments of the invention also apply to smaller or larger arrays of pixels. One skilled in the art will also recognize that pixel arrays may be arranged to form other and different pixel areas or groups than those discussed above.

Figure 8:
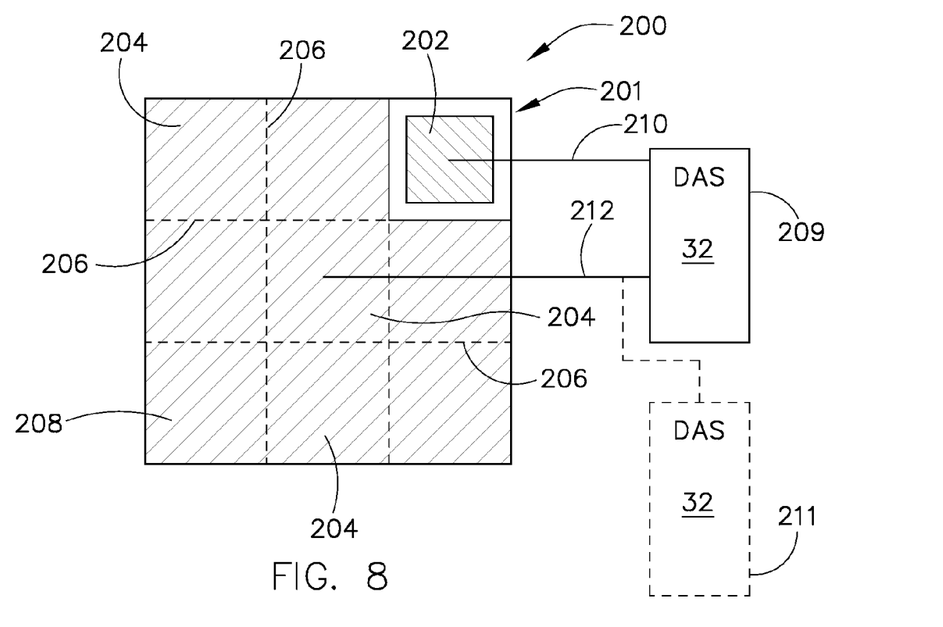
FIG. 8 illustrates several sub-pixels combined into one readout region and a separate sub-pixel in a second readout region according to an embodiment of the present invention.

Referring now to FIG. 8, a three-by-three array of pixels 200 is shown according to an embodiment of the present invention. Array 200 includes a first pixel 202 positioned near a corner 201 of array 200. A plurality of pixels 204 positioned in remaining locations of the array 200 are combined to form a large, single pixel 208. The array of pixels 200 may be positioned within a detector array, such as detector array 18 of FIGS. 1 and 2, and may be switched according to the embodiment illustrated in FIGS. 6 and 7.

By appropriately switching the array of pixels 200 in the fashion as illustrated in FIGS. 6 and 7, pixel 202 and pixel 208 may be separately read out thereby electrically separating pixel 202 from pixels 204. Electrical charges generated within pixel 202 are transmitted through electrical line 210 to a DAS 32. Likewise, electrical charges generated in pixel 108 are separately transmitted through electrical line 212 to DAS 32. As such, pixel 202 has a saturation flux threshold that is higher than a saturation flux threshold of the large, single pixel 208. However, because the pixels 204 have been combined into a large single pixel 208, the combined large pixel 208 has a smaller perimeter-to-area ratio than that of a single pixel, such as pixel 202. Accordingly, pixel 202 may have a larger amount of crosstalk as compared to that of pixel 208.

Figure 9:
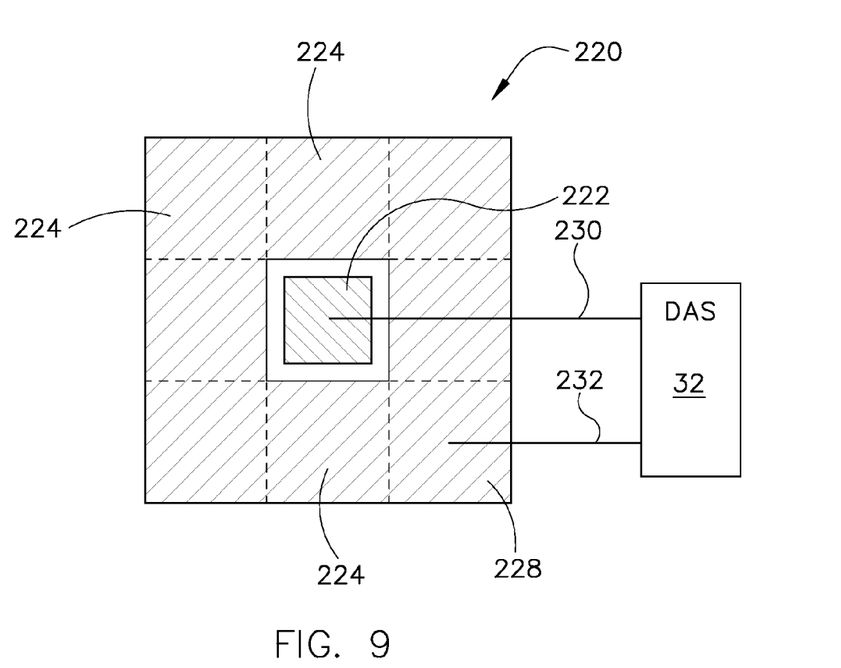
FIG. 9 illustrates several sub-pixels combined into one readout region and a separate sub pixel in a second readout region according to an embodiment of the present invention.

Referring now to FIG. 9, a three-by-three array of pixels 220 is shown according to an embodiment of the present invention. Array 220 includes a first pixel 222 centrally positioned in the array of pixels 220 and a plurality of pixels 224 positioned in remaining locations of the array 220 that are combined to form a large, single pixel 228. The array of pixels 220 may be positioned within a detector array, such as detector array 18 of FIGS. 1 and 2.

By appropriately switching the array of pixels 220 in the fashion as illustrated in FIGS. 6 and 7, electrical charges generated within pixel 222 may be separately transmitted through electrical line 230 to a DAS 32. Likewise, pixel 228 may be separately transmitted through electrical line 232 to DAS 32. As such, first pixel 222 may have a saturation flux that is higher than a saturation flux of the large, single pixel 228. However, because the pixels 224 have been combined into a large, single pixel 228, the combined pixels 224 have a smaller perimeter-to-area ratio than that of first pixel 222. Accordingly, first pixel 222 may have a larger amount of crosstalk as compared to that of pixel 228.

One skilled in the art would recognize that the number of combined and combinable pixels is not limited to the arrangements of pixels as illustrated in FIGS. 8 and 9. Rather, one skilled in the art would recognize that the number of pixels may be combined to optimize a tradeoff between at least an amount of saturation of detector elements and an amount of cross-talk. Accordingly, an array of pixels of a detector, such as detector 18 of FIGS. 1 and 2, may be arranged such that data may be acquired throughout the array at and between the extremes of high and low flux conditions.

Furthermore, the arrangement combination of pixels may be dynamic such that, depending on examination protocols, patient size, etc., saturation and cross-talk can be optimized for specific conditions, thus improving the overall flux capability of the system. At low flux rate, pixel elements may be combined to effectively form a large, single pixel element that may be binned into a single DAS channel. At progressively higher flux, the number of combined elements contributing to the channel output is reduced. At the highest flux setting, one pixel element is connected to each DAS channel. Thus, the level of binning is based on overall optimization DQE of the detector. Furthermore, as the flux alters during operation rate, it is possible to dynamically alternate or adjust the pixel binning arrangement in order to effect a spatial oversampling and increase the spatial resolution of the detector between acquired views.

Additionally, one skilled in the art would recognize that groups of pixels may be dithered, or interleaved and directed to different DAS ICs. As such, and as an example illustrated in FIG. 8, lines 210 and 212 may be directed to different DAS ICs (second DAS IC 211 shown in phantom) to minimize loss of contiguous blocks of data in the event of a lost IC. Separate groups of pixels need not be directed to input channels within the same DAS. In this fashion, in the event that a IC fails during the life of the product, if the readout channels are interleaved, a pattern may be selected to minimize a loss of data in large blocks. In other words, as illustrated in FIG. 8, if the first DAS 209 is caused to read channel 210 and the second DAS 211 is caused to read channel 212, then in the event that one of the DASs 209, 211 fails, the other one may still be available to gather data from a given region of a detector. Though some data may be lost, the overall loss may be mitigated by at least obtaining some data in the given region, though a loss of resolution may occur. One skilled in the art would recognize that ICs may have channels dithered in a pattern that will minimize loss of large blocks of data, thus enabling and optimizing the readout of data in the event that one or more ICs fails in the device.

Figure 10:
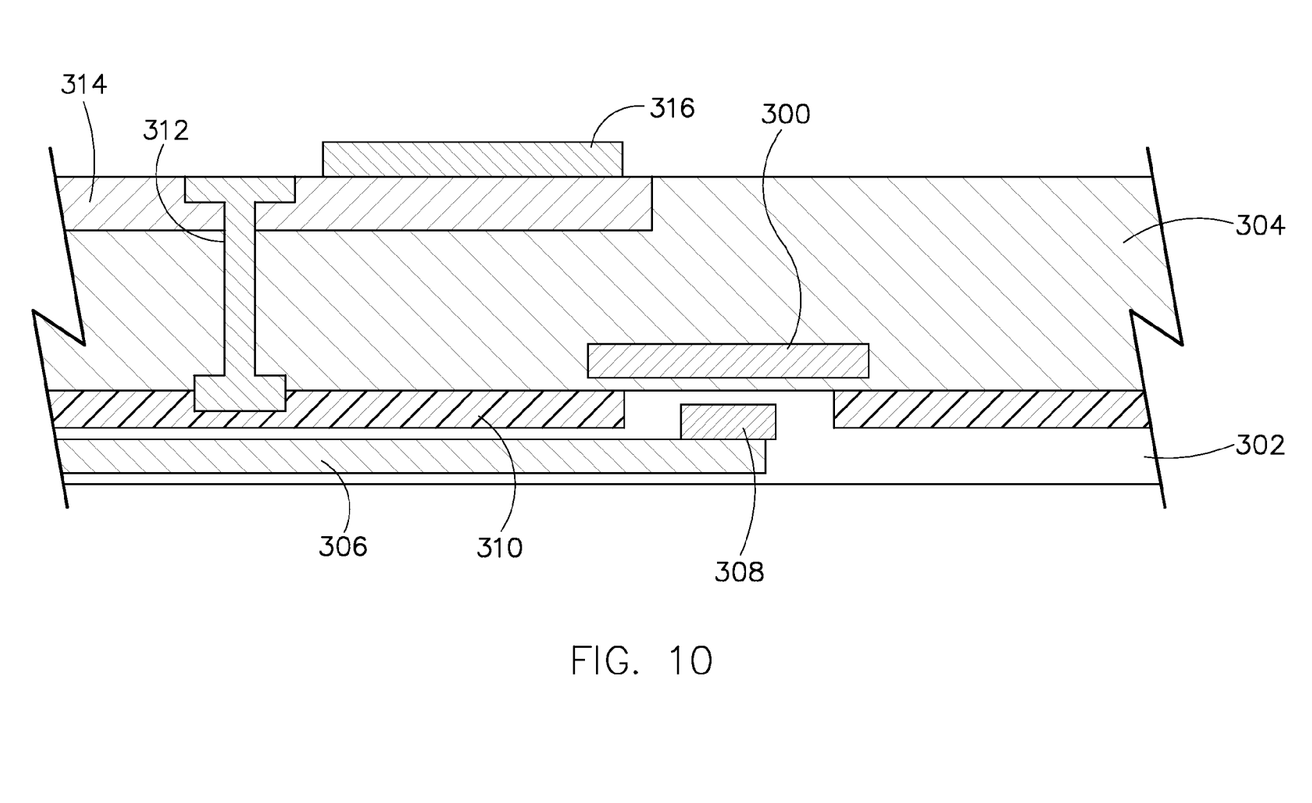
FIG. 10 illustrates a FET switch in a silicon interposer according to an embodiment of the present invention.

Referring now to FIG. 10, a FET switch 300 is illustrated in a semiconductor crystal interposer that may be incorporated into switches, such as switches 90-94 of FIGS. 6 and 7 according to an embodiment of the present invention. As illustrated, the FET switch is built into the interposer structure and may be positioned on the top, bottom, or within the interposer material itself. The semiconductor crystal may be formed from semiconductor materials such as silicon, GaAs, and the like. A semiconductor crystal formed from silicon includes the ability to use fine lithography and the capability of forming integrated FET switches therein.

Referring still to FIG. 10, FET switch 300 includes a deposited insulating layer 302 positioned on the surface of silicon 304. Gate control 306 is positioned within the insulating layer 302 and is connected to FET switch 300 through contact material 308. A first conductive material 310 is positioned on silicon 304, and a conductive path, or via 312 electrically connects the first conductive material 310 through silicon 304 to a second conductive material 314. Second conductive material 314 is also positioned on silicon 304, on a surface opposite that of where the first conductive material 310 is positioned. A pad, or contact 316 is positioned on, and in electrical contact with, the second conductive material 314. As such, pad 316 serves as a contact point for, for instance, an anode such as anode 62 as illustrated in FIG. 5. Accordingly, FET 300 may be operated through the use of gate control 310 such that FET 300 may be opened or closed, thus operating FET 300 as a switch according to embodiments of the present invention.

Figure 11:
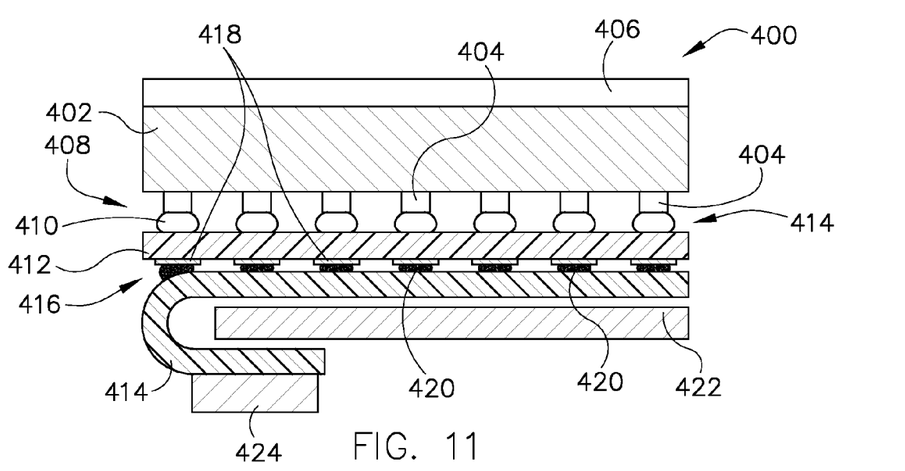
FIG. 11 illustrates an end view of a detector module according to an embodiment of the present invention.
Figure 12:
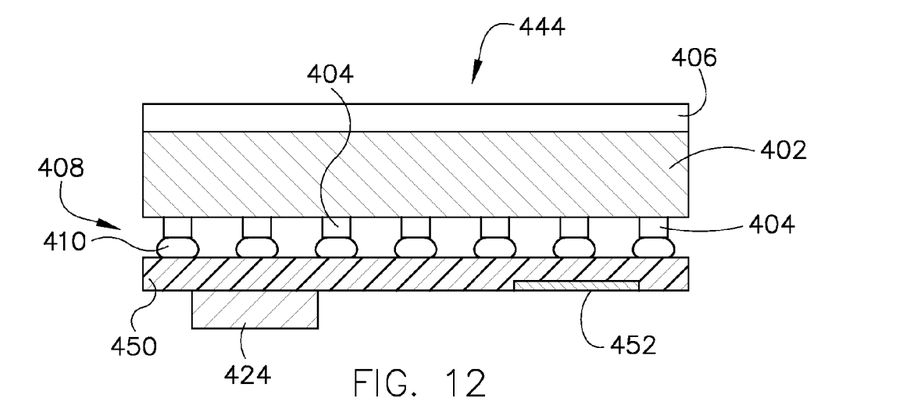
FIG. 12 illustrates an end view of a detector module according to an embodiment of the present invention
Figure 13:
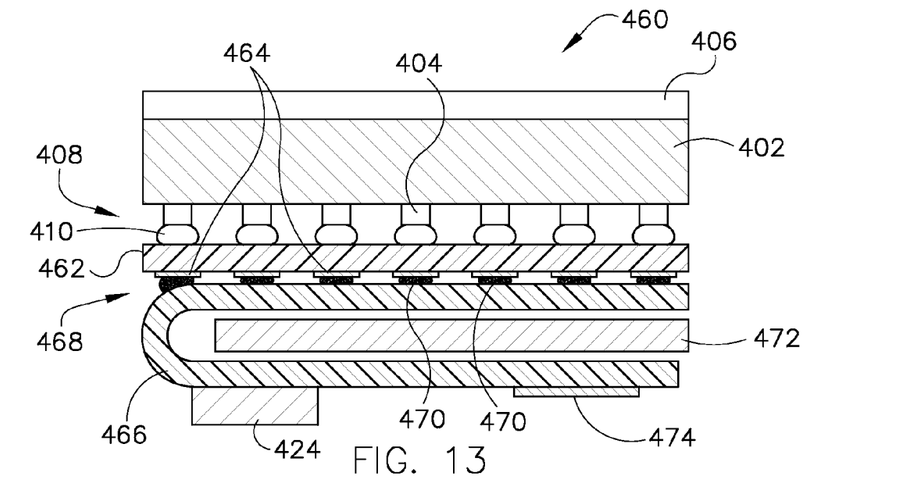
FIG. 13 illustrates an end view of a detector module according to an embodiment of the present invention

FIGS. 11-13 illustrate an end-view of alternate embodiments of a detector module 400 such as detector module 20 of FIG. 4. The detector module 400 includes a direct conversion layer 402 having a number of electronically pixelated structures or anodes 404 arranged in a 2D array 406 to define a number of detector elements, anodes, or contacts. The embodiments illustrated in FIGS. 11-13 include at least an interposer or redistribution layer positioned between the layer of anodes 404 and an ASIC of DAS 32. The embodiments illustrated also include switches for combining the number of pixels into larger effective pixel areas as described above.

FIG. 11 illustrates an end view of a portion of detector module 400 according to an embodiment of the present invention. In this embodiment, a direct conversion material 402 has mounted thereon a high voltage electrode 406. The direct conversion material 402 also has mounted thereon a 2D array 408 of anodes 404 that are electrically connected through bump-bonds 410 to an interposer 412 which has positioned thereon a pattern 414 of pads that are arranged in a matching pattern 408 of anodes 404. The attachment process for the bump bonds 410 may include, but is not limited to, low temperature solder, conductive epoxy, anisotropic conductive flex, and other means. The interposer 412 can be constructed from a semiconductor crystal layer, such as Si or GaAs, or as a layered composite structure with active elements such as FETs mounted separately thereon. As shown in the embodiment of FIG. 11, the interposer 412 is constructed according to the manner described above in FIG. 10 having switching elements such as switches 90-94 shown in FIGS. 6 and 7 formed therein that pass electrical signals to a flex circuit 414.

The interposer 412 has an array 416 of bond pads 418 and is electrically connected to the flexible circuit 414 having a matching array 416 of pads 418. In one embodiment, the bond pads 418 of interposer 412 are connected to the flex circuit 414 through bump bonds 420 which may include but are not limited to low temperature solder, conductive epoxy, anisotropic conductive flex, and other means. The flex circuit 414 is mounted on a substrate 422, which may include but is not limited to alumina, aluminum nitride, and beryllia. Other non-ceramic materials such as aluminum silicon carbide (AlSiC) and metal matrix composites may be used as well. Flex circuit 414 has mounted thereon a DAS readout device, or integrated circuit 424, and in this embodiment, the flex circuit 414 serves as a redistribution layer for distributing signals from the interposer 412 to the integrated circuit 424.

FIG. 12 illustrates an end view of a portion of detector 444 according to another embodiment of the present invention. In this embodiment, a direct conversion material 402 has mounted thereon a high voltage electrode 406. The direct conversion material 402 also has mounted thereon a 2D array 408 of anodes 404 that are electrically connected through bump bonds 410 to an interposer 450, which has positioned thereon a pattern 408 of pads that are arranged in a matching pattern 408 of anodes 404. The interposer 450 can be constructed from a semiconductor crystal layer, such as Si or GaAs, or as a layered composite structure with active elements. As shown in the embodiment of FIG. 12, switching elements 452, which includes switches such as switches 90-94 shown in FIGS. 6 and 7, are mounted on interposer 450. The switching elements illustrated at 452 may reside on the interposer 450 in a small area at any position within the interposer 450. The attachment process for the bump bonds 410 may include, but is not limited to, low temperature solder, conductive epoxy, anisotropic conductive flex, and other means. Interposer 450 has mounted thereon DAS integrated circuit 424, and in this embodiment, the interposer 450 serves as a redistribution layer for distributing signals from the interposer 450 to the DAS integrated circuit 424.

In one embodiment, switching elements 452 are positioned within direct conversion material 402 and the DAS integrated circuit 424 is attached thereto. In this embodiment electrical signals are routed within the direct conversion material 402 to the DAS integrated circuit 424, and the redistribution layer and switches are formed on the anode-side surface of the direct conversion material, thus integrating interposer 450 with the direct conversion material 402 to form a single monolithic overall structure.

FIG. 13 illustrates an end view of a portion of detector 460 according to another embodiment of the present invention. In this embodiment, a direct conversion material 402 has mounted thereon a high voltage electrode 406. The direct conversion material 402 also has mounted thereon a 2D array 408 of anodes 404 that are electrically connected through bump bonds 410 to an interposer 462 which has positioned thereon a pattern 408 of pads that are arranged in a matching pattern 408 of anodes 404. The interposer 462 can be constructed from a semiconductor crystal layer, such as Si or GaAs, or as a layered composite structure with active elements. The attachment process for the bump bonds 410 may include, but is not limited to, low temperature solder, conductive epoxy, anisotropic conductive flex, and other means.

The interposer 462 also has an array of bond pads 464 and is electrically connected to a flexible circuit 466 having a matching array 468 of pads. In one embodiment, the bond pads 464 of interposer 462 are connected to the array 468 of pads of flex circuit 466 through bump bonds 470 which may include but are not limited to low temperature solder, conductive epoxy, anisotropic conductive flex, and other means. The flex circuit 466 is mounted on a substrate 472, which may include but is not limited to a ceramic such as alumina, aluminum nitride, and beryllia, or may be of other non-ceramic material such as AlSiC and metal matrix composites. The flex circuit 466 may be constructed having switching elements 474, which includes switches such as switches 90-94 shown in FIGS. 6 and 7, mounted thereon that pass electrical signals from the interposer 462 to the DAS integrated circuit 424, which serves as a redistribution layer for distributing signals from the interposer 462 to the DAS integrated circuit 424. By positioning the switching elements 474 on the flex 466, and not on or within the interposer 462, the interposer 462 may then be fabricated as a passive multi-layer ceramic or organic material, such as FR4 or a printed wiring board, as is commonly understood in the art.

Figure 14:
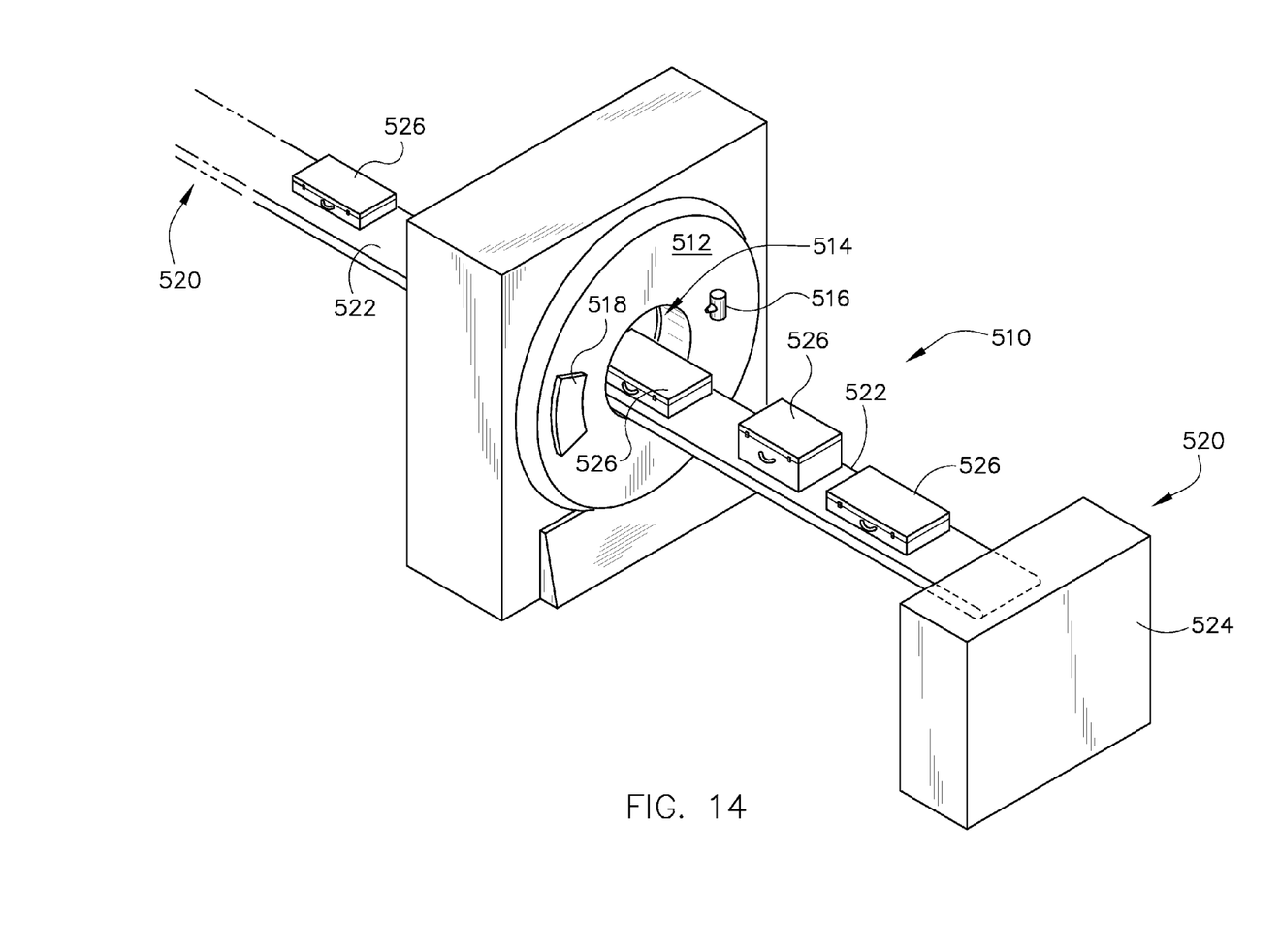
FIG. 14 illustrates when is a pictorial view of a CT system for use with a non-invasive package inspection system.

Referring now to FIG. 14, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having detector arrays comprised of cells similar to that shown in FIG. 4 or 5. A conveyor system 520 is also provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

Therefore, according to one embodiment of the present invention a CT detector includes a direct conversion material configured to generate electrical charge upon reception of x-rays, a plurality of metallized anodes configured to collect electrical charges generated in the direct conversion material, at least one readout device, and a redistribution layer having a plurality of electrical pathways configured to route the electrical charges from the plurality of metallized anodes to the at least one readout device. A plurality of switches is coupled to the plurality of electrical pathways between the plurality of metallized anodes and the at least one readout device, wherein each of the plurality of switches includes an input line electrically coupled to one of the plurality of metallized anodes, a first output node electrically coupled to the at least one readout device, and a second output node electrically coupled to at least one other switch of the plurality of switches.

In accordance with another embodiment of the present invention a method of fabricating a CT detector includes providing a direct conversion material, attaching a plurality of metallized anodes to the direct conversion material, electrically coupling an input of a first switch to a first anode of the plurality of metallized anodes, and electrically coupling a first output of the first switch to a second anode of the plurality of metallized anodes and to a first readout channel of a readout device.

Yet another embodiment of the present invention includes a CT system having a rotatable gantry having an opening to receive an object to be scanned. The CT system includes a high frequency electromagnetic energy projection source configured to project a high frequency electromagnetic energy beam toward the object and a detector positioned to receive x-rays that pass through the object. The detector includes a pair of electrical charge collectors having a gap therebetween, a direct conversion material electrically coupled to the pair of electrical charge collectors, and a readout device having a first input channel coupled to a switch, wherein a first output of the switch is configured to electrically connect one input channel of the readout device to the pair of electrical charge collectors.

The present invention has been described in terms of the preferred embodiment, and it is recognized that equivalents, alternatives, and modifications, aside from those expressly stated, are possible and within the scope of the appending claims.

What is claimed is:

1. An imaging detector comprising:
 a direct conversion material configured to generate electrical charge upon reception of x-rays;
 a plurality of metallized anodes coupled to the direct conversion material configured to collect electrical charges generated in the direct conversion material;
 at least one readout device;
 a redistribution layer having a plurality of electrical pathways configured to route the electrical charges from the plurality of metallized anodes to the at least one readout device;
 a silicon layer positioned between the redistribution layer and the plurality of metallized anodes;
 a flex circuit positioned between the silicon layer and the at least one readout device and having the electrical pathways therein; and
 a plurality of switches embedded in the silicon layer, the plurality of switches coupled to the plurality of electrical pathways between the plurality of metallized anodes and the at least one readout device, the plurality of switches comprising at least one via, wherein each of the plurality of switches comprises:
  an input line electrically coupled to one of the plurality of metallized anodes;
  a first output node electrically coupled to an input channel of the at least one readout device and the plurality of metallized anodes; and
  a second output node electrically coupled to at least one other switch of the plurality of switches.

2. The detector of claim 1 wherein the at least one other switch is electrically coupled to a neighboring metallized anode of the plurality of metallized anodes or to at least one readout device.

3. The detector of claim 1 wherein the plurality of switches are FETs.

4. The detector of claim 1 wherein the electrical charges are dithered, or interleaved and directed to different DAS ICs, between the plurality of metallized anodes and the at least one readout device.

5. The detector of claim 1 wherein the redistribution layer and switches are formed on an anode-side surface of the direct conversion material.

6. The detector of claim 1 wherein the redistribution layer comprises silicon.

7. The detector of claim 6 wherein the at least one readout device is attached to a surface of the silicon and wherein the plurality of switches is embedded in the silicon.

8. The detector of claim 6 further comprising a flex circuit having the electrical pathways therein, the flex circuit positioned at least partially between the silicon and the at least one readout device.

9. The detector of claim 8 wherein the plurality of switches is attached to a surface of the flex circuit and wherein the at least one readout device is mounted on a surface of the flex circuit.

10. The detector of claim 1 wherein the imaging detector is a CT imaging detector.

11. A method of fabricating a CT detector, the method comprising:
 providing a direct conversion material;

electrically coupling a plurality of metallized anodes to the direct conversion material;

electrically coupling an input of a first switch to a first anode of the plurality of metallized anodes;

electrically coupling a first output of the first switch to the plurality of metallized anodes and to an input channel of a readout device through a redistribution layer;

providing a silicon layer between the redistribution layer and the plurality of metallized anodes;

positioning a flex circuit between the silicon layer and the readout device, the flex circuit having a plurality of electrical pathways therein; and providing a plurality of switches embedded in the silicon layer, the plurality of switches coupled to the plurality of electrical pathways between the plurality of metallized anodes and the readout device, and the plurality of switches comprising at least one via.

12. The method of claim 11 further comprising electrically coupling a second output of the first switch to a second readout channel of the readout device.

13. The method of claim 12 further comprising:
electrically coupling an input of a second switch to a third anode of the plurality of metallized anodes; and
electrically coupling a first output of the second switch to a second anode of the plurality of metallized anodes and to a first readout channel of a readout device.

* * * * *